United States Patent
Kappler (10) Patent No.: US 9,869,779 B2
(45) Date of Patent: Jan. 16, 2018

(54) OPTIMIZED SIGNAL DETECTION BY QUANTUM-COUNTING DETECTORS

(71) Applicant: Siemens Aktiengesellschaft, München (DE)

(72) Inventor: Steffen Kappler, Effeltrich (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 7 days.

(21) Appl. No.: 14/932,466

(22) Filed: Nov. 4, 2015

(65) Prior Publication Data

US 2016/0131771 A1    May 12, 2016

(30) Foreign Application Priority Data

Nov. 10, 2014 (DE) .................. 10 2014 222 855

(51) Int. Cl.
| | |
|---|---|
| G01T 1/24 | (2006.01) |
| G01T 1/29 | (2006.01) |
| A61B 6/03 | (2006.01) |
| A61B 6/00 | (2006.01) |

(52) U.S. Cl.
CPC ............ *G01T 1/243* (2013.01); *G01T 1/2928* (2013.01); *A61B 6/032* (2013.01); *A61B 6/42* (2013.01)

(58) Field of Classification Search
None
See application file for complete search history.

(56) References Cited

U.S. PATENT DOCUMENTS

| | | | |
|---|---|---|---|
| 9,025,004 B2 * | 5/2015 | Midavaine | ........... G02B 27/017 348/36 |
| 2009/0122956 A1 | 5/2009 | Janssen et al. | |
| 2012/0326049 A1 | 12/2012 | Hannemann et al. | |
| 2013/0156285 A1 | 6/2013 | Hayashida | |

FOREIGN PATENT DOCUMENTS

| | | |
|---|---|---|
| DE | 102007033462 A1 | 1/2009 |
| DE | 102011077859 A1 | 12/2012 |

OTHER PUBLICATIONS

German Office Action thereof dated Oct. 21, 2015.

* cited by examiner

*Primary Examiner* — Edwin Gunberg
(74) *Attorney, Agent, or Firm* — Harness, Dickey & Pierce, P.L.C.

(57) ABSTRACT

A method is described for setting the detection of a macropixel signal of an x-ray detector with a plurality of pixels, each combined to form at least one macropixel. The geometrical efficiency and the signal drift factor of the individual pixels are first established. A target drift value is established. A parameter, which sets a compromise between an allowed drift of the macropixel signals and the achievable dose efficiency, is also defined. Based on the established parameters, the weighting of the individual pixel signals, taking into account a function taking account of the signal drift and the dose utilization of the resulting macropixel signal depending on the weightings of the pixel signals, is established. A weighted addition of the individual pixel signals to form macropixel signals is defined on the basis of the weightings. A signal detection device, an x-ray detector and a computed tomography system are also described.

12 Claims, 5 Drawing Sheets

FIG 1  Prior art

OPTIMIZED SIGNAL DETECTION BY QUANTUM-COUNTING DETECTORS

PRIORITY STATEMENT

The present application hereby claims priority under 35 U.S.C. §119 to German patent application number DE 102014222855.7 filed Nov. 10, 2014, the entire contents of which are hereby incorporated herein by reference.

FIELD

At least one embodiment of the invention generally relates to a method for setting the detection of a macropixel signal of an x-ray detector with a plurality of pixels, which are each combined into at least one macropixel and detect individual signals in each case. At least one embodiment of the invention also generally relates to a method for detecting a macropixel signal of an x-ray detector with a plurality of pixels, which are each combined into at least one macropixel and detect individual signals in each case. Furthermore, at least one embodiment of the invention generally relates to a signal detection device for detecting a macropixel signal of an x-ray detector with a plurality of pixels, which are each combined into at least one macropixel and detect individual signals in each case. At least one embodiment of the invention further generally relates to an x-ray detector. Finally, at least one embodiment of the the invention generally relates to a computed tomography system.

BACKGROUND

X-ray detectors are used in medical examinations, for example in computed tomography recordings with the aid of x-ray radiation. These x-ray detectors can be embodied as scintillator detectors or detectors with direct converters. An x-ray detector is to be understood below as any type of detector, which detects either x-rays or other hard rays, such as Gamma rays for example.

In a detector made of a scintillator material the scintillator material is excited during the passage of the x-ray radiation and the excitation energy is emitted again in the form of light. This visible light created in the material is measured with the aid of photodiodes. The scintillator detector is embodied as a rule as a type of array comprising a number of scintillator elements, wherein the scintillator elements are assigned individual photodiodes, so that the photodiodes likewise form an array.

Detectors with direct converters on the other hand feature semiconductor materials which undertake a direct conversion into an electrical signal of the radiation striking them. The x-ray radiation striking the detectors directly creates charge carriers in the form of electron-hole pairs. By application of a voltage (bias voltage) to the semiconductor material, the charge carrier pairs are separated by the electrical field created thereby and reach electrical contacts or electrodes, which are attached to the semiconductor material (see FIG. 1). Through this an electrical charge pulse is created, which is proportional to the absorbed energy and is evaluated by downstream readout electronics. Semiconductor detectors employed in the area of human-medical imaging, based on CdTe or CdZnTe for example, have the advantage compared to the scintillator detectors generally used today in this area, that an energy-sorting counting is possible with them, i.e. the detected x-ray quanta can be divided up, as a function of their energy for example, into two classes (high-energy and low-energy) or into a number of classes.

During the operation of semiconducting, direct-converting radiation detectors, such as for example detectors based on CdTe or CZT, the phenomenon of polarization occurs during irradiation by Gamma and x-ray radiation, especially at high intensities. This manifests itself in an unwanted change of the internal electrical field in the semiconductor material of the detector. Because of the polarization, the charge carrier transport characteristics and thereby also the detector characteristics change. In particular the said changes lead to a change of the signal characteristics of the measurement signal as a function of the time. In other words, because of the polarization, the intensity of the measurement signal changes over time, with the radiation dose remaining the same. This phenomenon is also called signal drift. A detector is constructed from a plurality of pixels. Since the signal drift of the individual pixels is different, a distribution of the signal drift factors assigned to the individual pixels exists for the detector. Over time or under irradiation respectively this distribution changes, wherein the breadth of the distribution of the signal drift factors increases much more strongly than the average value of this distribution.

One possibility of reducing the signal drift consists of making use of the fact that the breadth of the distribution of the signal drift factors grows more strongly than the change in the average value of the distribution. In this case a number of detectors are combined into groups of individual pixels, so-called macropixels. These macropixels can comprise a number of 2×2, 3×3 or 4×4 individual pixels for example. In order to reduce the signal drift, individual pixels which are drifting strongly are completely excluded from the signal transmission. In this way an improved drift behavior of the detector signal is achieved. However this improvement comes at the expense of a very great deterioration in the efficiency of the detector, i.e. a signal utilization reduced by for example 6.25% to 25% and thus also a correspondingly worsened signal-to-noise ratio (SNR) or a worsened dose utilization.

SUMMARY

The inventors recognized that a problem resides in obtaining a detector signal with limited signal drift and at the same time good dose utilization (or SNR).

At least one embodiment is directed to a method for setting a macropixel signal of an x-ray detector; a method for detecting a macropixel signal of an x-ray detector; a signal detection device; an x-ray detector; and a computed tomography system.

In an embodiment of the inventive method for detecting a macropixel signal of an x-ray detector with a plurality of pixels, which are each combined into at least one macropixel and detect individual signals in each case, a weighted addition of the individual pixel signals to form macropixel signals is carried out, wherein weightings defined in advance are used. To set these weightings, first of all parameters relating to the geometrical efficiency and the signal drift factor of the individual pixels are established and also a target drift value is defined. Subsequently a step for limiting the signal drift is performed, wherein the best possible dose efficiency is obtained. This is achieved by minimizing a function which takes into account both the signal drift and also the dose utilization (or the SNR) of the resulting macropixel signal while varying the weightings of the individual pixel signals. The relative contribution of signal drift and dose utilization (or SNR) to the function can be set by a freely-selectable parameter λ. Finally the weighted addition mentioned at the start of the individual pixel signals to form macropixel signals based on the established weightings is carried out. In this case the geometrical efficiency depends on the example scattering of the size of the individual pixels.

An embodiment of the inventive signal detection device for detecting a macropixel signal of an x-ray detector with a plurality of pixels, which are each combined into at least one macropixel and detect individual signals in each case, has a parameter establishing unit for establishing the geometrical efficiency of the individual pixels, the signal drift factors of the individual pixels and also a target drift value. The individual parameters can be established and defined for example by a test measurement. The target drift value and the free parameter λ can be predetermined by the user or a definition unit. The maximum acceptable signal drift can be defined by the user for example and transferred to the signal drift definition unit. An embodiment of the inventive signal detection device also has an optimization unit for establishing the weightings of the individual pixel signals, taking into account a function which takes account of both the signal drift and also the dose utilization (or SNR) of the resulting macropixel signal as a function of the weightings of the pixel signals. Finally the inventive signal detection device has a signal weighting unit for weighted addition of the individual pixel signals to form macropixel signals on the basis of the established weightings.

An embodiment of the inventive x-ray detector has the signal detection device.

An embodiment of the inventive computed tomography system has an embodiment of the inventive x-ray detector.

BRIEF DESCRIPTION OF THE DRAWINGS

The invention is explained in greater detail once again below on the basis of example embodiments, which refer to the enclosed figures. Here the same components are provided with identical reference characters in the different figures. Generally the figures are not true-to-scale. In the figures.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In an embodiment of the inventive method for detecting a macropixel signal of an x-ray detector with a plurality of pixels, which are each combined into at least one macropixel and detect individual signals in each case, a weighted addition of the individual pixel signals to form macropixel signals is carried out, wherein weightings defined in advance are used. To set these weightings, first of all parameters relating to the geometrical efficiency and the signal drift factor of the individual pixels are established and also a target drift value is defined. Subsequently a step for limiting the signal drift is performed, wherein the best possible dose efficiency is obtained. This is achieved by minimizing a function which takes into account both the signal drift and also the dose utilization (or the SNR) of the resulting macropixel signal while varying the weightings of the individual pixel signals. The relative contribution of signal drift and dose utilization (or SNR) to the function can be set by a freely-selectable parameter $\lambda$. Finally the weighted addition mentioned at the start of the individual pixel signals to form macropixel signals based on the established weightings is carried out. In this case the geometrical efficiency depends on the example scattering of the size of the individual pixels.

In an embodiment of the inventive method for detecting a macropixel signal of an x-ray detector with a plurality of pixels, which are each combined into at least one macropixel and detect individual signals in each case, first of all, as a type of calibration process, an embodiment of the inventive method for setting the detection of a macropixel signal of an x-ray detector is performed. Subsequently, in the actual measurement process of a radiation dose, signals from a plurality of pixels are detected and the detected signals are combined into a macropixel by a weighted addition of the signals with the aid of the established weightings. The macropixel signal advantageously adheres to a previously defined upper limit of a signal drift and, as a result of taking account of the dose utilization (or the SNR) in the definition of the weighting of the individual pixel signals as described, achieves an improved dose utilization, i.e. the dose efficiency of the arrangement is improved.

An embodiment of the inventive signal detection device for detecting a macropixel signal of an x-ray detector with a plurality of pixels, which are each combined into at least one macropixel and detect individual signals in each case, has a parameter establishing unit for establishing the geometrical efficiency of the individual pixels, the signal drift factors of the individual pixels and also a target drift value. The individual parameters can be established and defined for example by a test measurement. The target drift value and the free parameter λ can be predetermined by the user or a definition unit. The maximum acceptable signal drift can be defined by the user for example and transferred to the signal drift definition unit. An embodiment of the inventive signal detection device also has an optimization unit for establishing the weightings of the individual pixel signals, taking into account a function which takes account of both the signal drift and also the dose utilization (or SNR) of the resulting macropixel signal as a function of the weightings of the pixel signals. Finally an embodiment of the inventive signal detection device has a signal weighting unit for weighted addition of the individual pixel signals to form macropixel signals on the basis of the established weightings.

An embodiment of the inventive x-ray detector has the signal detection device.

An embodiment of the inventive computed tomography system has an embodiment of the inventive x-ray detector.

A majority of the components of an embodiment of the inventive signal detection device mentioned above, especially the parameter establishing unit, the signal drift definition unit, the optimization unit and also the signal weighting unit, can be realized wholly or in part in the form of software modules in a processor of the signal detection device or a corresponding control device. This is advantageous to the extent that control devices already present can be upgraded by a software installation to carry out the inventive method. The invention therefore also comprises a computer program product, which is able to be loaded directly into a processor of the computed tomograph, with program code means for carrying out all steps of the inventive method (also in accordance with the aspects described below), when the program product is executed on the computed tomograph.

Further especially advantageous embodiments and developments of the invention emerge from the dependent claims and also the description given below. In this case, an embodiment of the inventive signal detection device or an embodiment of the inventive x-ray detector and the inventive computed tomography system can also be further developed in a similar manner to the dependent method claims.

In a preferred embodiment of the inventive method for setting the detection of a macropixel signal of an x-ray detector, the target drift value is defined as the value zero. In this embodiment a drift of the macropixel signal is prevented.

In an especially preferred embodiment of the inventive method the function which takes account of both the signal drift and also the dose utilization of the resulting macropixel signal is optimized. Thus, in this embodiment, taking into account a maximum signal drift to be tolerated, the dose efficiency is reduced to the minimum which, for the given signal drift, produces a macropixel signal with optimal signal strength and optimal signal-to-noise ratio.

In an especially preferred variant of the inventive method the function which takes into account both the signal drift and also the dose utilization (or the SNR) of the resulting macropixel signal is formulated as follows:

$$f(w_i) = \lambda \left( \frac{\sum_{i=1}^{l} d_i \cdot e_i \cdot w_i}{\sum_{i=1}^{l} e_i \cdot w_i} - t \right)^2 + \left( \frac{\sqrt{\sum_{i=1}^{l} e_i \cdot w_i^2}}{\sum_{i=1}^{l} e_i \cdot w_i} \cdot \sqrt{\sum_{i=1}^{l} e_i} - 1 \right)^2 \quad (1)$$

In this equation $e_i$ defines the geometrical efficiency and $d_i$ defines the signal drift factor of the individual pixel signals. The parameter t represents the target drift value of the macropixel signal and λ sets the compromise of signal drift and dose utilization (or SNR) of the resulting macropixel signal. The weightings to be established of the individual pixel signals are represented by $w_i$. The variable l specifies the number of individual pixels per macropixel.

In an especially practicable embodiment of the inventive x-ray detector the macropixels comprise a group of 4, 9 or 16 individual pixels.

Figure 1:
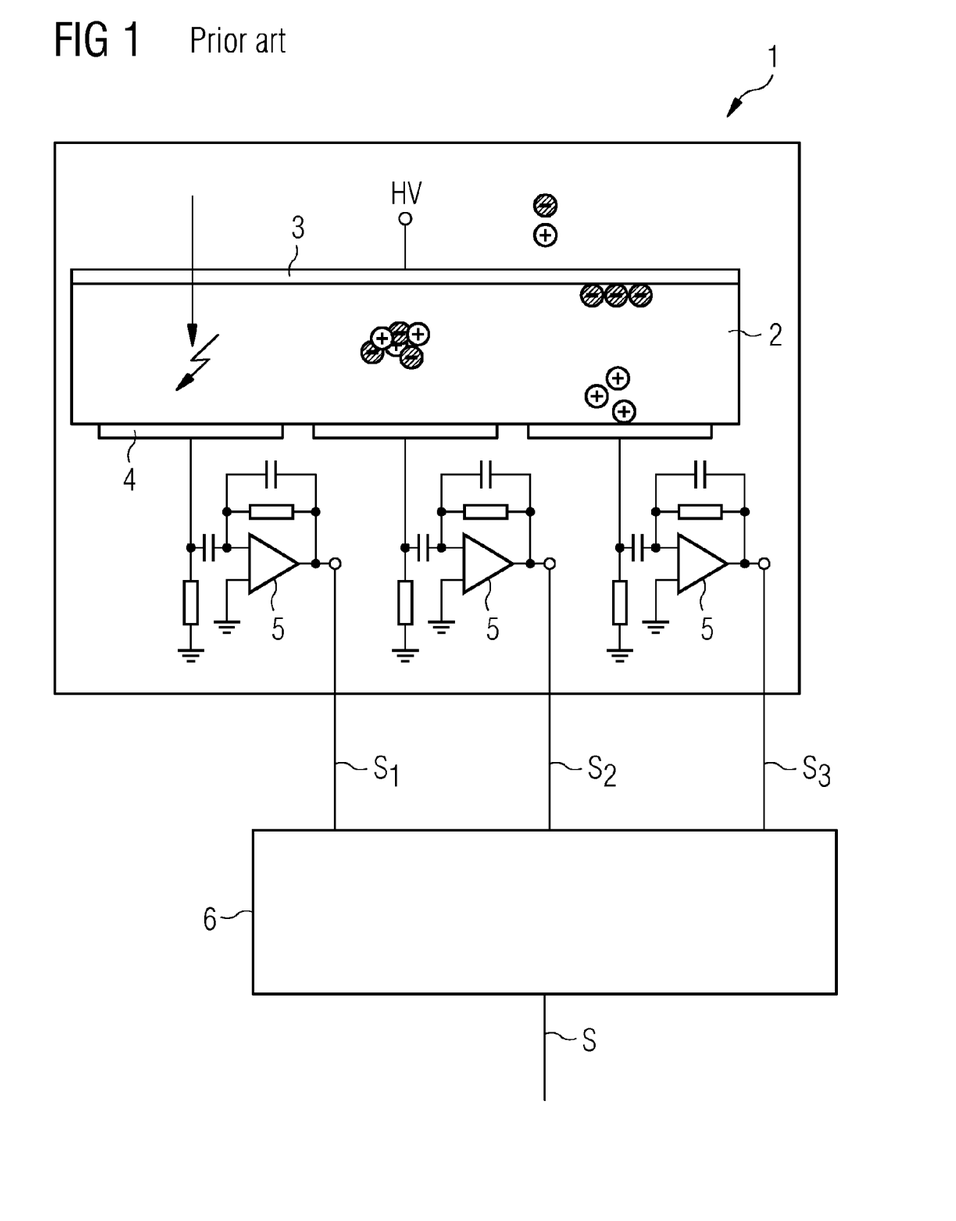
FIG. 1 shows schematically the structure of a conventional x-ray detector, which is constructed as a direct converter.

FIG. 1 shows the cross section of a conventional semiconductor detector 1, which functions as a direct converter. The semiconductor detector 1 is embodied as a planar pixel detector. It comprises semiconductor material 2 in the form of a single crystal as detector material. The semiconductor material is covered on one side by a metal surface, which forms an electrical backside contact 3. A voltage HV is present at the backside contact 3.

The opposite side of the single crystal 2 is covered by a structured metallization, the individual part surfaces of which are embodied as pixel contacts 4 and in their totality form a pixel matrix. The size and the spacings of the pixel contacts 4, together with further material parameters of the semiconductor material 2, determine the maximum local resolution capability of the detector 1. The resolution usually lies in the range between 10 and 500 μm. The individual pixel contacts 4 are each connected to separate readout electronics circuits 5, with which measurement signals s1, s2, s3 are detected.

Furthermore the detector includes an addition element 6, with which the measurement signals s1, s2, s3 are combined into one macropixel signal S.

It is pointed out that the arrangement 1 in FIG. 1 is shown as a cross-section and therefore the arrangement 1 in FIG. 1 comprises a total of 9 pixel contacts. For better clarification, corresponding to the cross-sectional view, only 3 pixel contacts per macropixel have been included. As already mentioned, 4, 16 or another number of pixel contacts per macropixel are usual.

The detector 1 shown in FIG. 1 functions as follows: X-ray radiation falling on the detector 1 brings about interactions of the x-ray quanta with the semiconductor material 2 of the detector 1, wherein electron-hole pairs are created. The voltage HV applied to the contacts of the detector creates an electrical field, which moves the created charge carriers towards the electrical contacts, especially towards the pixel contacts 4. The charge concentration at the electrodes or pixel contacts 4 of the detector 1 creates an electrical charge pulse, which is proportional to the absorbed energy of the x-ray radiation. This charge pulse is read out by the connected readout electronics 5. The pixel signals s1, s2, s3 detected by the readout electronics 5 are forwarded to an addition unit 6, which combines the measurement signals s1, s2, s3 (actually the measurement signals s1 to s9) to form a macropixel signal S.

Figure 2:
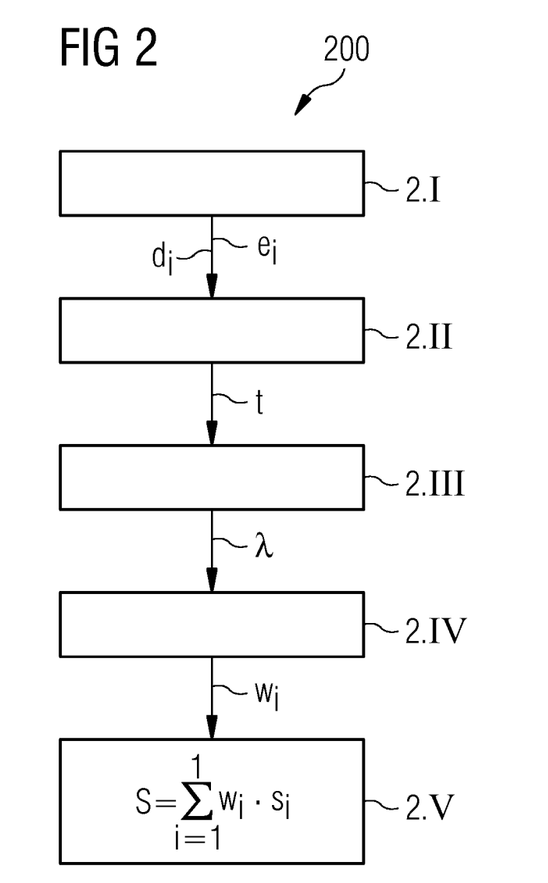
FIG. 2 shows a flow diagram, which schematically shows a method in accordance with the example embodiment.

FIG. 2 shows a flow diagram, which shows a method 200 for setting the detection of a macropixel signal S of an x-ray detector with a plurality of pixels, which are combined in each case to form at least one macropixel, in accordance with an example embodiment of the invention.

In step 2.I parameters such as the geometrical efficiency $e_i$ and the signal drift factor $d_i$ of the individual pixels 4 are established. The geometrical efficiency is associated with the surface of the individual pixels. The signal drift factor is produced by the following formula:

$$d_i = 1 - \frac{s_0 - s_1}{s_0} \quad (2)$$

In this equation s0 is the signal strength of a signal from a pixel at time t0 and s1 is the signal strength of a signal from the pixel at time t1. The establishment of the said parameters can be done experimentally for example by a calibration measurement.

In step 2.II a target drift value t is established or defined. This can for example be a drift value which corresponds to the average values of all individual pixels in the entire x-ray detector. It is also possible to set the target drift value to the preferred value of zero.

In step 2.III the parameter λ is set, which regulates the compromise between signal drift and dose utilization (or SNR) of the resulting macropixel signal. This parameter can be defined by a person skilled in the art for example.

In step 2.IV the weighting wi of the individual pixel signals is established, taking into account a function taking account of both the signal drift and also the dose utilization (or the SNR) of the resulting macropixel signal, which represents a function depending on the weighting wi of the pixel signals. To put it more precisely, in the example embodiment illustrated, a function reflecting the reduction of the dose utilization of the incident x-ray radiation, which is formulated by equation 1, is minimized. The minimization can be carried out by means of known minimization methods. Examples of such minimization methods are Downhill Simplex or stochastic minimization.

Finally, in step 2.V the actual x-ray measurement or imaging of a part region of an examination object is carried out, wherein, during the addition of the individual pixel signals si to macropixel signals, a weighting based on the established weightings wi is carried out.

Thus, in concrete terms, the macropixel signals S are calculated in accordance with the following formula.

$$S = \sum_{i=1}^{I} w_i \cdot s_i \quad (3)$$

Through the optimized weighting of the individual pixel signals, a good dose efficiency is obtained, while at the same time limiting the drift of the signals of the macropixels. The method is applied for a number n of macropixels accordingly for all of the n macropixels.

Figure 3:
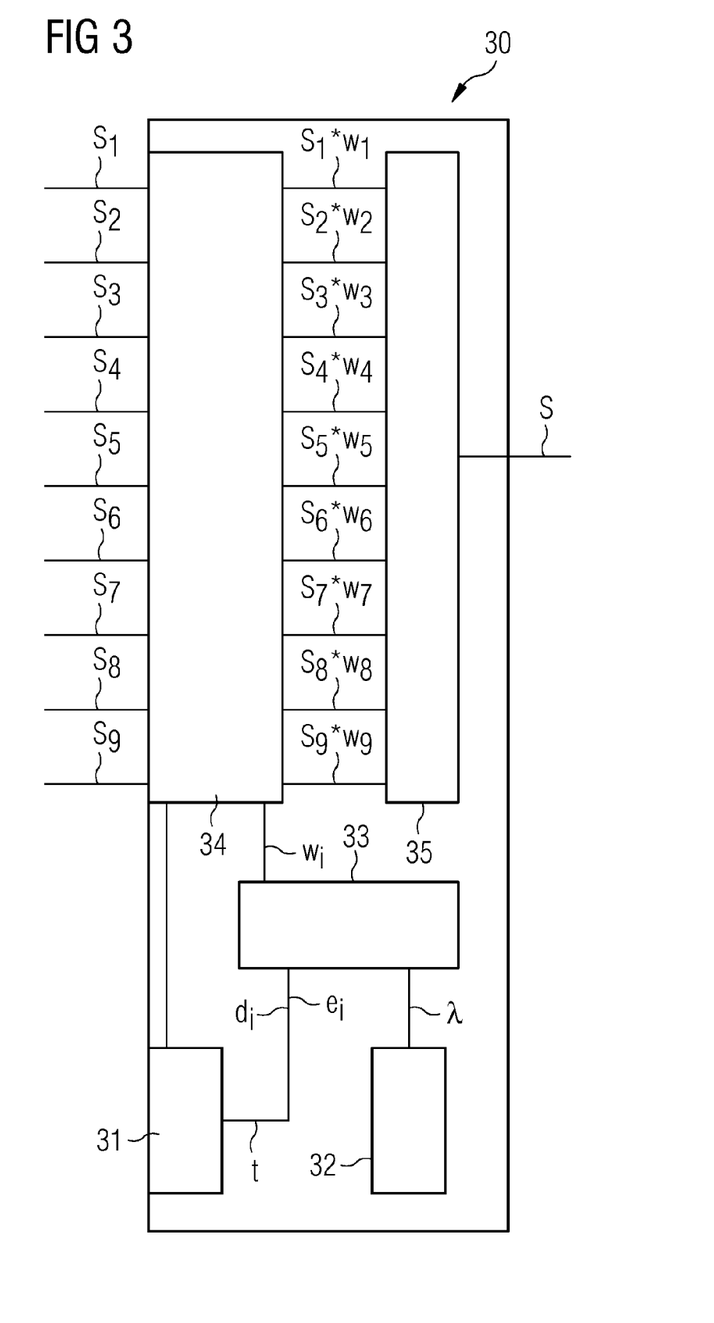
FIG. 3 shows a block diagram, which schematically shows the structure of a signal detection device in accordance with an example embodiment of the invention.

FIG. 3 shows schematically the structure of a signal detection device 30 in accordance with an example embodiment of the invention. The signal detection device 30 is illustrated by way of example for the detection of the signals of 9 pixels, which together form one macropixel. The signal detection device 30 comprises a parameter establishing unit 31 for establishing the geometrical efficiency ei, the signal drift factor di of the individual pixels 4 and a target drift value t. The target drift value can be freely selected. The said values can be determined experimentally. The detector in such cases has a defined radiation dose applied to it for example and, from the individual signals si detected in such cases and from the change over time of these signals, the said parameters are deduced. A signal drift definition unit 32 defines a parameter λ, which represents a compromise between an allowed drift of the macropixel signals S and the dose utilization (or SNR). The parameter λ and also the target drift value t can also be predetermined externally, i.e. by the user.

An optimization unit 33 receives the established and defined parameter values from the parameter establishing unit 31 and from the drift definition unit 32 and establishes a weighting wi of the individual pixel signals si, taking into account a function f(wi) which takes account of both the signal drift and also the dose utilization (or the SNR) of the resulting macropixel signal (see equation 1), which represents a function depending on the weightings wi of the individual pixel signals si.

A signal weighting unit 34 weights the signals si of the individual pixels 4 detected during the actual measurement of an x-ray radiation dose. In this process the individual pixel signals si are multiplied by the weightings wi established by the optimization unit 33.

The weighted signals si*wi are subsequently added by a summation unit 35 to form a macropixel signal S in accordance with equation 3.

Figure 4:
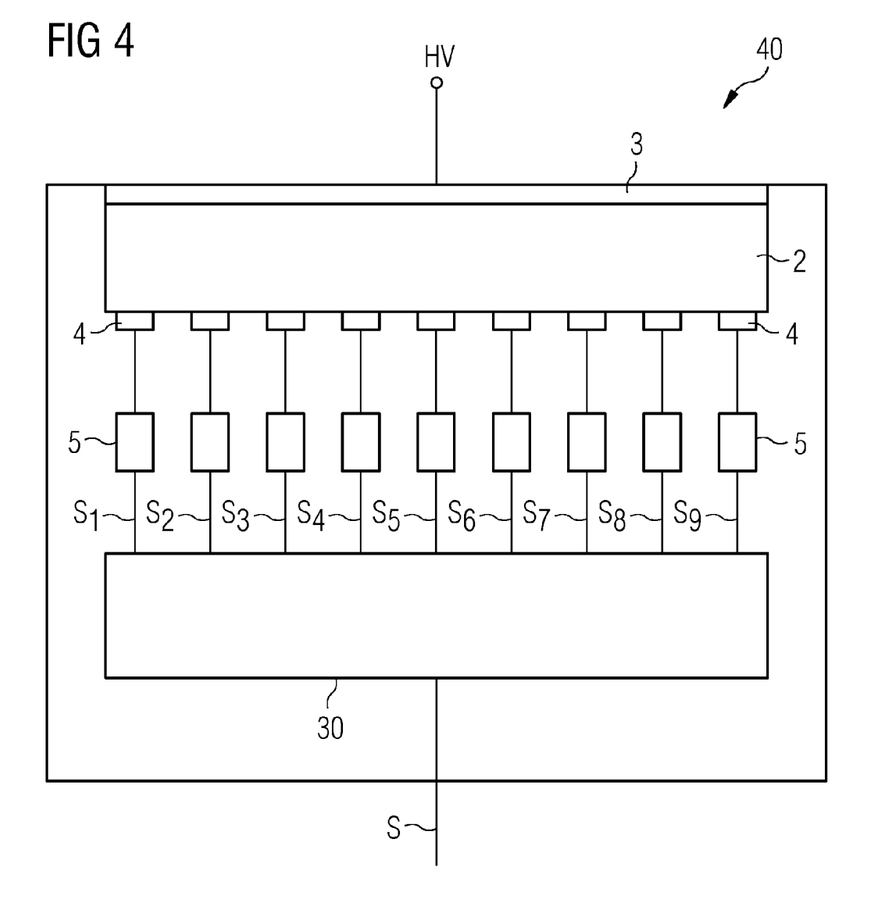
FIG. 4 shows the structure of an x-ray detector in accordance with an example embodiment of the invention.

In FIG. 4 an x-ray detector 40 in accordance with an example embodiment of the invention is shown schematically with only one macropixel. Naturally detectors have a plurality of macropixels in practice. Thus in practice either each of the macropixels is assigned to one of the described signal detection devices 30 or one signal detection device 30 detects a plurality of macropixel signals by multiplexing.

The x-ray detector 40 shown in FIG. 4 comprises semiconductor material 2 in the form of a single crystal as detector material. The semiconductor material is covered on one side with a metal surface, which forms an electrical backside contact 3. A voltage HV is present at the backside contact.

The opposite side of the single crystal 2 is covered by a structured metallization, the individual part surfaces of which are embodied as pixel contacts 4 and in their totality form a pixel matrix. The size and the spacings of the pixel contacts 4, together with further material parameters of the semiconductor material 2, determine the maximum local resolution capability of the detector 1. The individual pixel contacts 4 are each connected to separate readout electronics circuits 5, with which measurement signals S1 . . . S9 are detected.

Furthermore the detector 40 comprises an inventive signal detection device 30, with which the measurement signals S1 . . . S9 are weighted according to the inventive method and are combined to form a macropixel signal S. Subsequently the macropixel signal S is combined with other macropixel signals S, if the detector has a plurality of macropixels, to form raw data RD (not shown).

Figure 5:
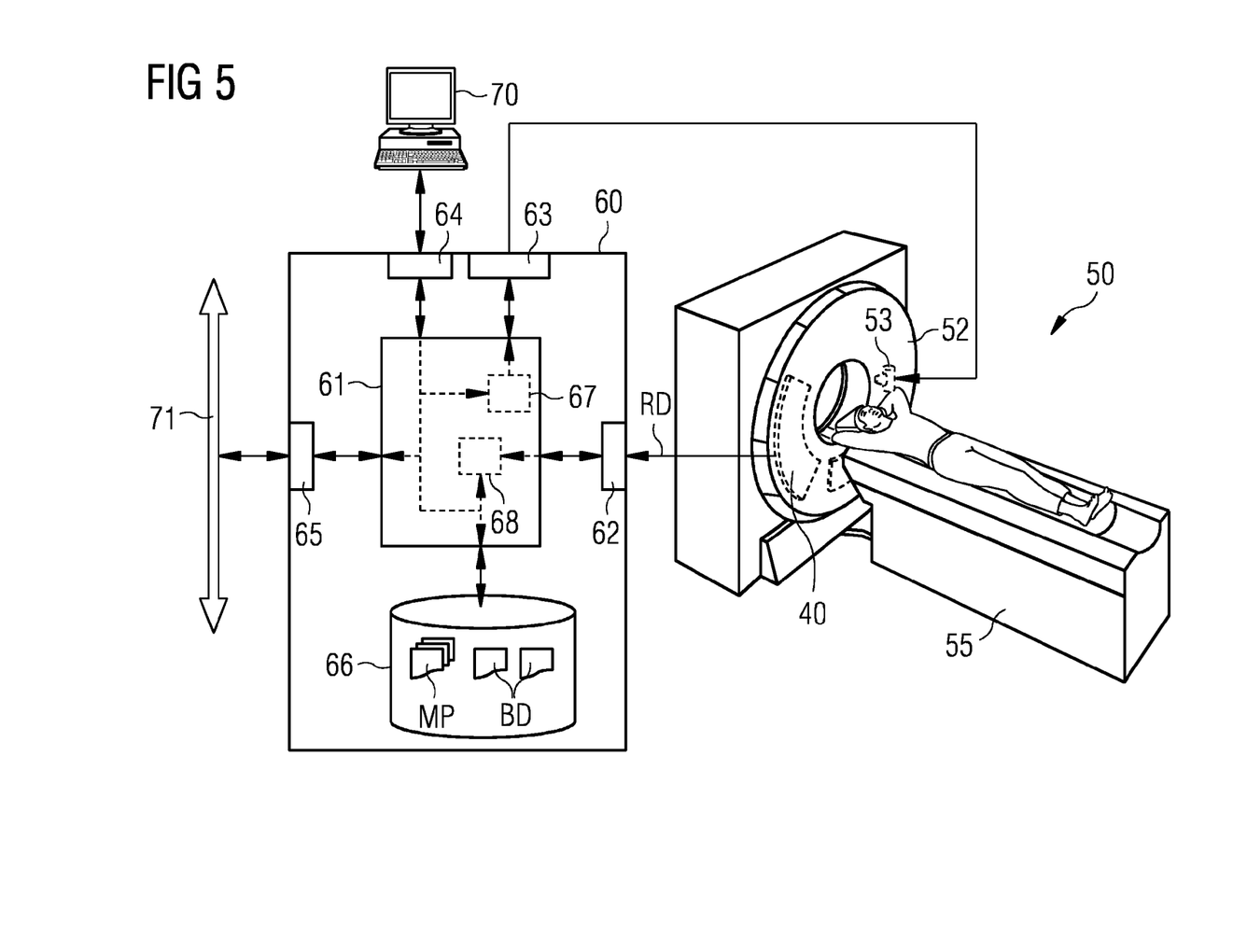
FIG. 5 shows schematically the structure of a computed tomography system in accordance with an example embodiment of the invention.

FIG. 5 shows a rough schematic diagram of a computed tomography system 50 in accordance with an example embodiment of the invention, which has the inventive x-ray detector 40. In the usual way the computed tomography system 50 has a scanner 52 with a gantry, in which an x-ray source 53 rotates, which irradiates a patient in each case, who is pushed by means of a couch 55 into a measurement space of the gantry, so that the radiation strikes an inventive detector 40 lying opposite the x-ray source 53 in each case. It is expressly pointed out that the example embodiment in accordance with FIG. 5 only involves one example of a CT and the invention can also be used on any given CT constructions, for example with annular, fixed x-ray detectors and/or a number of x-ray sources.

The computed tomography system 50 also has a control device 60. Basically these types of CT systems and associated control devices are known to the person skilled in the art and therefore do not need to be explained in detail.

One component of the control device 60 is a processor 61, on which various components are realized in the form of software modules. The control device 60 also has a terminal interface 64, to which a terminal 70 is connected, via which an operator can operate the control device 60 and thus the computed tomography system 50. A further interface 65 is a network interface for connection to a data bus 71, in order to establish a connection to an RIS or PACS in this way. Via this bus 71 measurement request commands can be received for example and can then be selected by means of the terminal 70, for a measurement to be carried out for example.

The scanner 52 can be activated by the control device 60 via a control interface 63, i.e. the speed of rotation of the gantry, the movement of the patient couch 55 and the x-ray source 53 itself are controlled for example. The raw data RD is read out from the detector 40 via an acquisition interface 62. Furthermore the control device 60 has a memory unit 66, in which items such as different measurement protocols MP are held.

One of the items implemented as a software component on the processor 61 is a measurement control unit 67. This measurement control unit 67 activates the scanner 52 via the control interface 63 on the basis of one or more selected measurement protocols MP, which may possibly have been modified by the operator via the terminal 70, in order to carry out a measurement and to acquire data.

A further component on the processor 61 is an image data reconstruction unit 68, with which the desired image data is reconstructed from the raw data RD obtained via the data acquisition interface 62. The reconstructed image data BD can then be held in the memory unit 66 or can be buffered for example. It can also be transferred immediately or later from the memory unit 66 via the data bus 71 to diagnosis stations, mass storage units or other output units and workstations, i.e. it can ultimately be passed to the PACS.

Preferably the subcomponents of an embodiment of the inventive signal detection device 30 are installed in the detector 40. As an alternative however, parts of this signal detection device 30, such as the parameter establishing unit 31, the signal drift definition unit 32, the optimization unit 33 and also the signal weighting unit 34 can be realized entirely or in part in the form of software modules in a processor of the control device 60 or can be stored in an associated memory or on the terminal 70.

In conclusion it is pointed out once again that the method and devices described in detail here involve example embodiments and that the basic principle can also be varied in wide areas by the person skilled in the art, without departing from the area of the invention, provided it is specified by the claims. Thus, as already explained, the signal detection device 30, instead of being realized in the detector 40, could also be realized as part of the control device 60 of a computed tomography system 50 or could be realized as software in a process system assigned to the detector 40 or the control device 60 of a computed tomography system 50. For the sake of completeness it is also pointed out that the use of the indefinite article "a" or "an" does not exclude the features involved also being able to be present a number of times. Likewise the term "unit" does not exclude said unit consisting of a number of components, which if necessary can also be distributed spatially.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. §112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating a reconstructed image of a region of a patient based on macropixel signals of an x-ray detector including a plurality of pixels, each of the plurality of pixels combined into at least one macropixel, the method comprising:
   establishing weightings of individual pixel signals from the plurality of pixels as a function of signal drift factors for the individual pixel signals, a target drift value for a resulting macropixel signal, dose utilization of the resulting macropixel signal and a geometrical efficiency of the plurality of pixels;
   generating the macropixel signals according to weighted sums of the individual pixel signals using the established weightings; and
   generating the reconstructed image of the region of the patient based on the generated macropixel signals.

2. The method of claim 1, wherein the target drift value is zero.

3. A non-transitory computer readable medium, loadable directly into a memory of a computed tomography system, including program code sections for out carrying the method of claim 2.

4. The method of claim 1, wherein the function is formulated as:

$$f(w_i) = \lambda \left( \frac{\sum_{i=1}^{l} d_i \cdot e_i \cdot w_i}{\sum_{i=1}^{l} e_i \cdot w_i} - t \right)^2 + \left( \frac{\sqrt{\sum_{i=1}^{l} e_i \cdot w_i^2}}{\sum_{i=1}^{l} e_i \cdot w_i} \cdot \sqrt{\sum_{i=1}^{l} e_i} - 1 \right)^2$$

wherein $e_i$ is the geometrical efficiency of the plurality of pixels, $d_i$ is a signal drift factor, and $t$ is the target drift value, $\lambda$ is a user-defined value indicative of a compromise between an allowed signal drift of the generated macropixel signals and an achievable dose efficiency, $\omega_i$ represents the weightings of the individual pixel signals and l specifies the number of pixels combined to form a macropixel.

5. The method of claim 1, further comprising:
   detecting the individual pixel signals from the plurality of pixels; and
   combining the detected individual pixel signals by weighted addition of the detected individual pixel signals with the aid of the established weightings, to generate the macropixel signals.

6. A non-transitory computer readable medium, loadable directly into a memory of a computed tomography system, including program code sections for carrying out the method of claim 5.

7. A non-transitory computer readable medium, loadable directly into a memory of a computed tomography system, including program code sections for carrying out the method of claim 1.

8. An image reconstruction device for reconstructing an image of a region of a patient based on macropixel signals of an x-ray detector including a plurality of pixels, each of the plurality of pixels combined to form at least one macropixel, the image reconstruction device comprising:
   at least one processor configured to execute computer-readable instructions to
      establish weightings of individual pixel signals from the plurality of pixels of the x-ray detector as a function of signal drift factors for the individual pixel signals, a target drift value for a resulting macropixel signal, dose utilization of the resulting macropixel signal and a geometrical efficiency of the plurality of pixels;
      generate the macropixel signals by performing weighted addition of the individual pixel signals using the established weightings; and
      generate the reconstructed image of the region of the patient based on the generated macropixel signals.

9. An x-ray detector comprising the image reconstruction device of claim 8.

10. The x-ray detector of claim 9, wherein the at least one macropixel includes a group of 9 or 16 individual pixels.

11. A computed tomography system comprising the x-ray detector of claim 10.

12. A computed tomography system comprising the x-ray detector of claim 9.

* * * * *